(12) United States Patent
Kreitenberg

(10) Patent No.: US 8,907,304 B2
(45) Date of Patent: Dec. 9, 2014

(54) ULTRAVIOLET AUTONOMOUS TROLLEY FOR SANITIZING AIRCRAFT

(71) Applicant: Arthur Kreitenberg, Los Angeles, CA (US)

(72) Inventor: Arthur Kreitenberg, Los Angeles, CA (US)

( * ) Notice: Subject to any disclaimer, the term of this patent is extended or adjusted under 35 U.S.C. 154(b) by 0 days.

(21) Appl. No.: 13/779,635

(22) Filed: Feb. 27, 2013

(65) Prior Publication Data
US 2014/0241941 A1    Aug. 28, 2014

(51) Int. Cl.
*A61L 2/10*    (2006.01)
*B64D 11/00*    (2006.01)

(52) U.S. Cl.
CPC ............... *A61L 2/10* (2013.01); *B64D 11/0007* (2013.01); *A61L 2202/16* (2013.01); *A61L 2202/25* (2013.01)
USPC ......................................... 250/492.1; 422/24

(58) Field of Classification Search
CPC ....................................................... A61L 2/10
USPC .......... 422/24, 292, 186.3; 250/455.11, 492.1
See application file for complete search history.

(56) References Cited

U.S. PATENT DOCUMENTS

| | | |
|---|---|---|
| 5,338,169 A | 8/1994 | Buckley |
| 5,369,892 A | 12/1994 | Dhaemers |
| 5,673,918 A | 10/1997 | Bigari |
| 5,959,423 A | 9/1999 | Nakanishi et al. |
| 6,311,974 B1 | 11/2001 | Koga |
| 6,370,453 B2 | 4/2002 | Sommer |
| 6,389,639 B1 | 5/2002 | Worsham |
| 6,419,190 B1 | 7/2002 | Nguegang |
| 6,565,668 B1 | 5/2003 | Sandberg et al. |
| 6,779,714 B2 | 8/2004 | Webb |
| 6,787,782 B1 | 9/2004 | Krosney et al. |
| 6,889,449 B2 | 5/2005 | Silver |
| 6,992,301 B2 | 1/2006 | Fenc |
| 7,204,208 B2 | 4/2007 | Johnson et al. |
| 7,459,695 B2 * | 12/2008 | Hanley et al. ............ 250/455.11 |
| 7,462,849 B2 | 12/2008 | Ferres et al. |
| 7,523,692 B1 | 4/2009 | Burns |
| 8,029,739 B2 | 10/2011 | Field et al. |
| 8,105,532 B2 * | 1/2012 | Harmon et al. ................. 422/24 |
| 8,193,515 B2 | 6/2012 | Kreitenberg |
| 8,226,887 B2 | 7/2012 | Harmon et al. |
| 8,330,121 B2 | 12/2012 | Douglas |

(Continued)

FOREIGN PATENT DOCUMENTS

| | | | |
|---|---|---|---|
| CN | 2621044 Y | * | 6/2004 |
| CN | 101756678 | | 6/2010 |

(Continued)

OTHER PUBLICATIONS

English language machine translation of CN 2621044 Y, published Jun. 2004.*

(Continued)

*Primary Examiner* — Sean E Conley
(74) *Attorney, Agent, or Firm* — Greenberg Traurig LLP

(57) ABSTRACT

A mobile body is configured to travel over a surface inside an aircraft cabin. A source of UV radiation is mounted to the mobile body and configured to direct UV radiation to the surface at a predetermined dosage. At least two articulated arms are mounted to the mobile body, and UV lamps mounted respectively on the arms. The mobile body is a trolley or cart for negotiating an aircraft aisle.

20 Claims, 11 Drawing Sheets

(56) References Cited

U.S. PATENT DOCUMENTS

| | | |
|---|---|---|
| 2004/0056201 A1 | 3/2004 | Fink et al. |
| 2004/0244138 A1 | 12/2004 | Taylor et al. |
| 2005/0022844 A1 | 2/2005 | Field et al. |
| 2005/0159275 A1 | 7/2005 | Bullman et al. |
| 2006/0216193 A1 | 9/2006 | Johnson et al. |
| 2007/0158499 A1 | 7/2007 | Whittingham |
| 2008/0056933 A1 | 3/2008 | Moore et al. |
| 2008/0184518 A1 | 8/2008 | Taylor et al. |
| 2009/0193676 A1 | 8/2009 | Shengguang et al. |
| 2010/0028201 A1 | 2/2010 | Neister |
| 2011/0082668 A1 | 4/2011 | Escrig et al. |
| 2011/0167574 A1 | 7/2011 | Stout et al. |
| 2012/0221192 A1 | 8/2012 | Seibt |
| 2012/0223216 A1 | 9/2012 | Flaherty et al. |
| 2013/0000675 A1 | 1/2013 | Hong et al. |
| 2013/0270459 A1 * | 10/2013 | Fontani ............... 250/492.1 |
| 2014/0044590 A1 | 2/2014 | Trapani |

FOREIGN PATENT DOCUMENTS

| | | |
|---|---|---|
| DE | 3937706 | 5/1991 |
| GB | 2391799 | 2/2004 |
| JP | H1057614 | 3/1998 |
| JP | 2000325059 | 11/2000 |
| JP | 2005013723 | 1/2005 |
| JP | 2007082747 | 4/2007 |
| JP | 2009291349 | 12/2009 |
| WO | WO 2008/010684 A1 | 1/2008 |
| WO | WO 2014/036217 A2 | 3/2014 |

OTHER PUBLICATIONS

European Search Report for European Patent Application No. EP14155515, completed on May 23, 2014 in Munich.

* cited by examiner

ULTRAVIOLET AUTONOMOUS TROLLEY FOR SANITIZING AIRCRAFT

BACKGROUND

The present disclosure is generally directed to a sanitation device and, more particularly, to a sanitation device that includes a source of ultraviolet (UV) radiation that is used to sanitize a surface. Additional embodiments of the present disclosure are directed to methods of sanitizing surfaces using the device.

This disclosure further concerns sanitizing aircraft, particularly aircraft cabins.

A system and method trolley intended to sanitize the air and surfaces in an aircraft cabin that are commonly contacted by passengers in an effort to minimize the risk of disease spread.

Infectious disease transmission among air travelers is a significant personal and public health concern. Common and potentially serious viral (e.g. Influenza), bacterial (e.g. Methicillin Resistant Staph aureus), and fungal pathogens are typically spread through the air and from mutually contacted surfaces, known as "fomites". Commercial aircraft currently use extensive on-board air filtration and ultraviolet "C" band (UVC) (extrinsic to cabin compartment) technologies to decrease airborne microbes, yet disease transmission continues, suggesting cabin surfaces may play a role.

UVC is an effective germicidal technology not only for air, but for surfaces. However, there is no currently available technology to effectively and efficiently sanitize the surfaces of a passenger aircraft interior. The aircraft interior is never exposed to natural ultraviolet light. Chemical disinfection is labor intensive, with potential harmful residues. Human exposure to UVC can be associated with skin and eye damage and care must be exercised in its use.

SUMMARY

The present disclosure generally relates to a sanitation device for sanitizing surfaces. In accordance with one embodiment of the disclosure, the sanitization device includes a mobile body and a source of UV radiation. The source of UV radiation is mounted to the mobile body, which is configured to travel over a surface. The source of UV radiation is configured to direct UV radiation to the surface at a dosage sufficient to diminish microbial loads to acceptable levels. Some distinguishing features of the current disclosure include:

A trolley for negotiating aircraft or similar aisles.
Two arms, that are:
Laden with UVC sources situated to disperse in a plurality of directions
Articulated to be laterally extensible over the seat backs and retractable within the trolley footprint.
Motor controlled and actuated.
Variably extensible, depending upon the seating configuration.
Programmable, depending upon the seating configuration.
Able to Function independent of each other.

One utility of this disclosure is self-evident on an intermittent basis in commercial domestic and international routine travel. In the extreme case of a bioterror threat of dispersing particularly lethal microbes via aircraft, this disclosure has the potential of preventing mass casualties.

The current disclosure provides a rapid, safe and effective means of sanitizing the cabin interior by exposure to germicidal UV-C light during routine ground fueling, and maintenance.

Additional and further objects, features, and advantages of the present disclosure will be readily apparent to those skilled in the art.

Other features and benefits that characterize embodiments of the present disclosure will be apparent upon reading the following detailed description and review of the associated drawings.

DESCRIPTION

Figure 1:
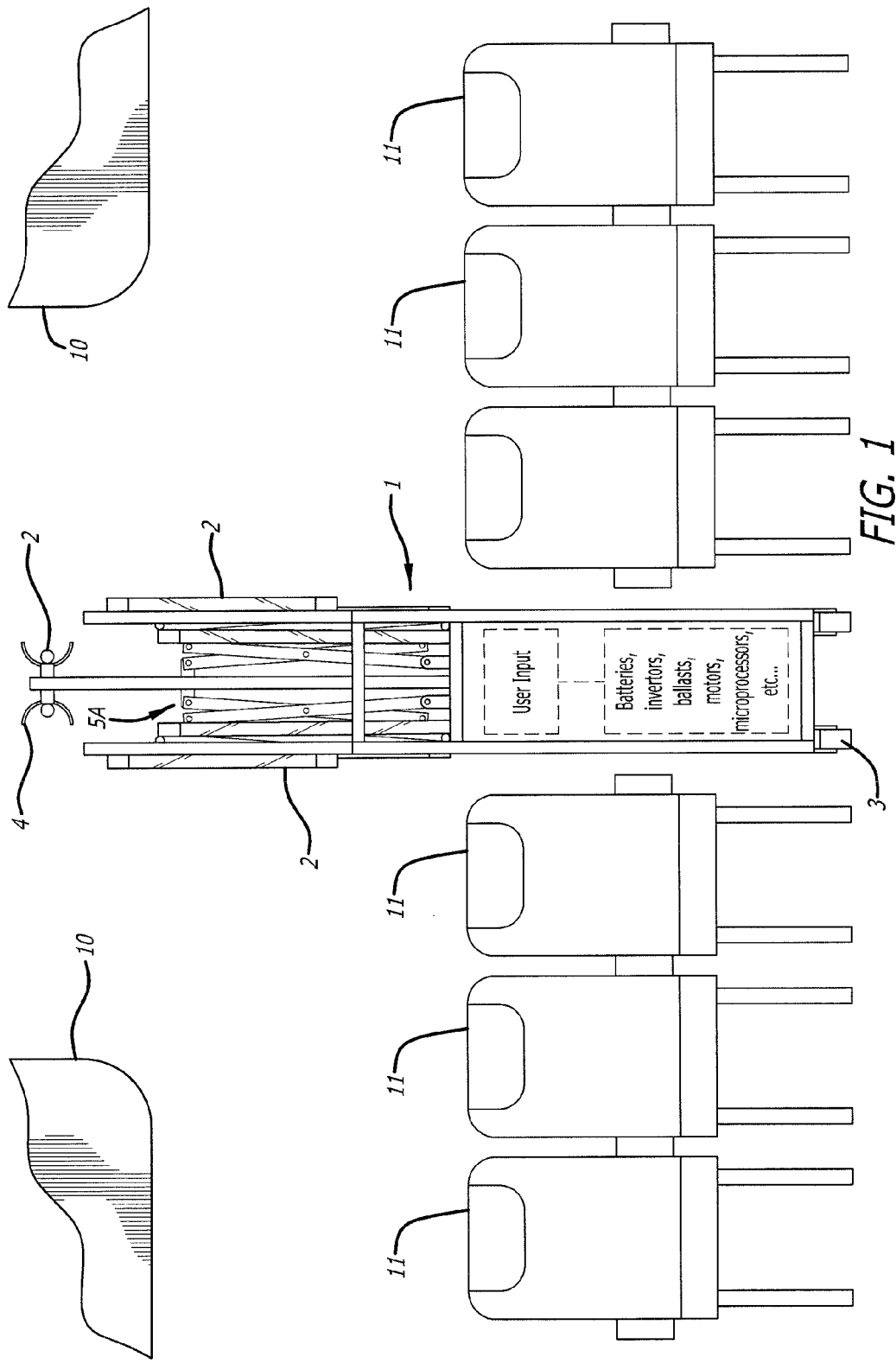
FIG. 1: Front View of Trolley with Arms Embodiment 1 in Stowed/Retracted Positions.
Figure 2:
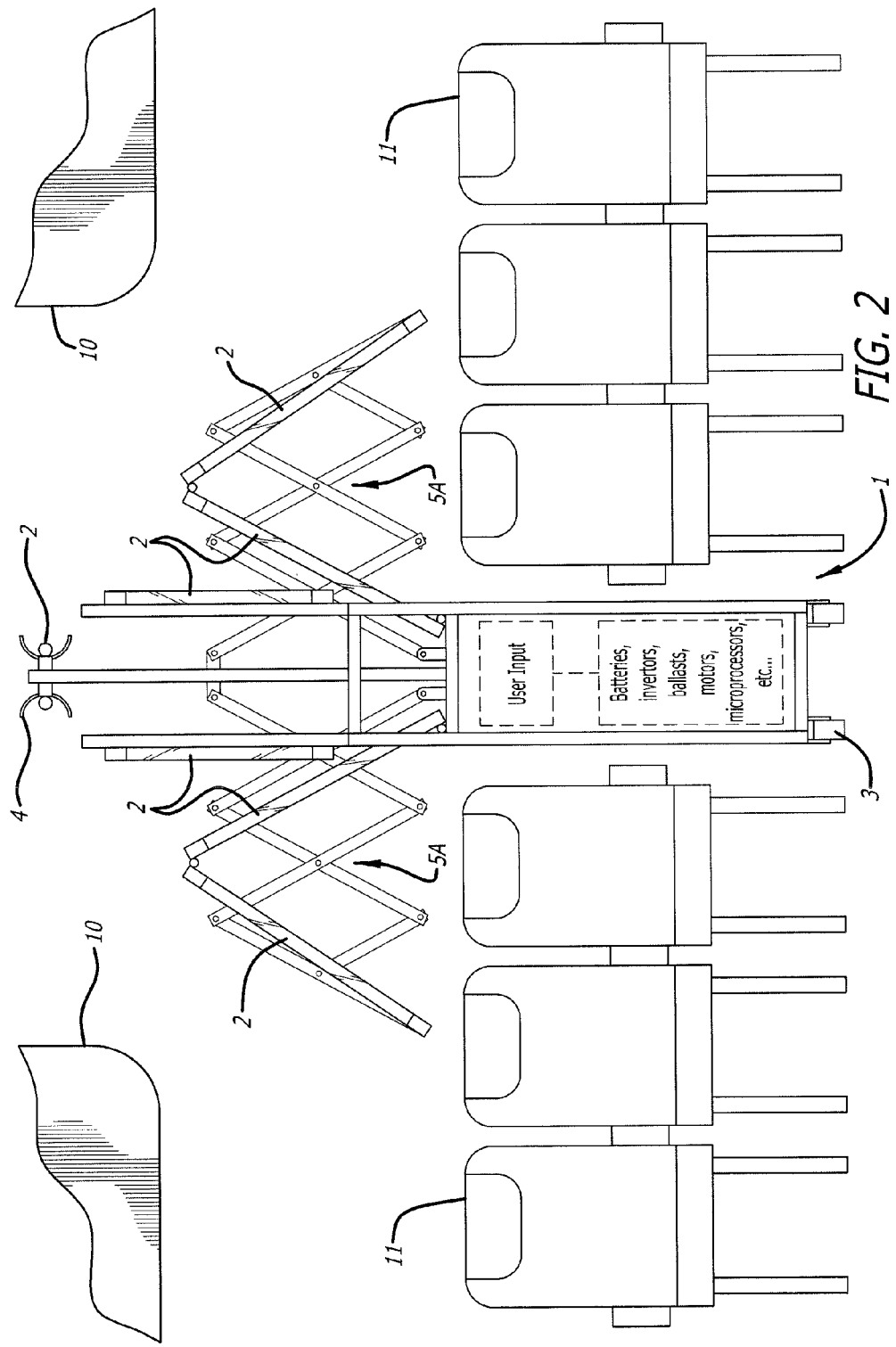
FIG. 2: Front View of Trolley with Arms Embodiment 1 in Partially Extended Positions.
Figure 3:
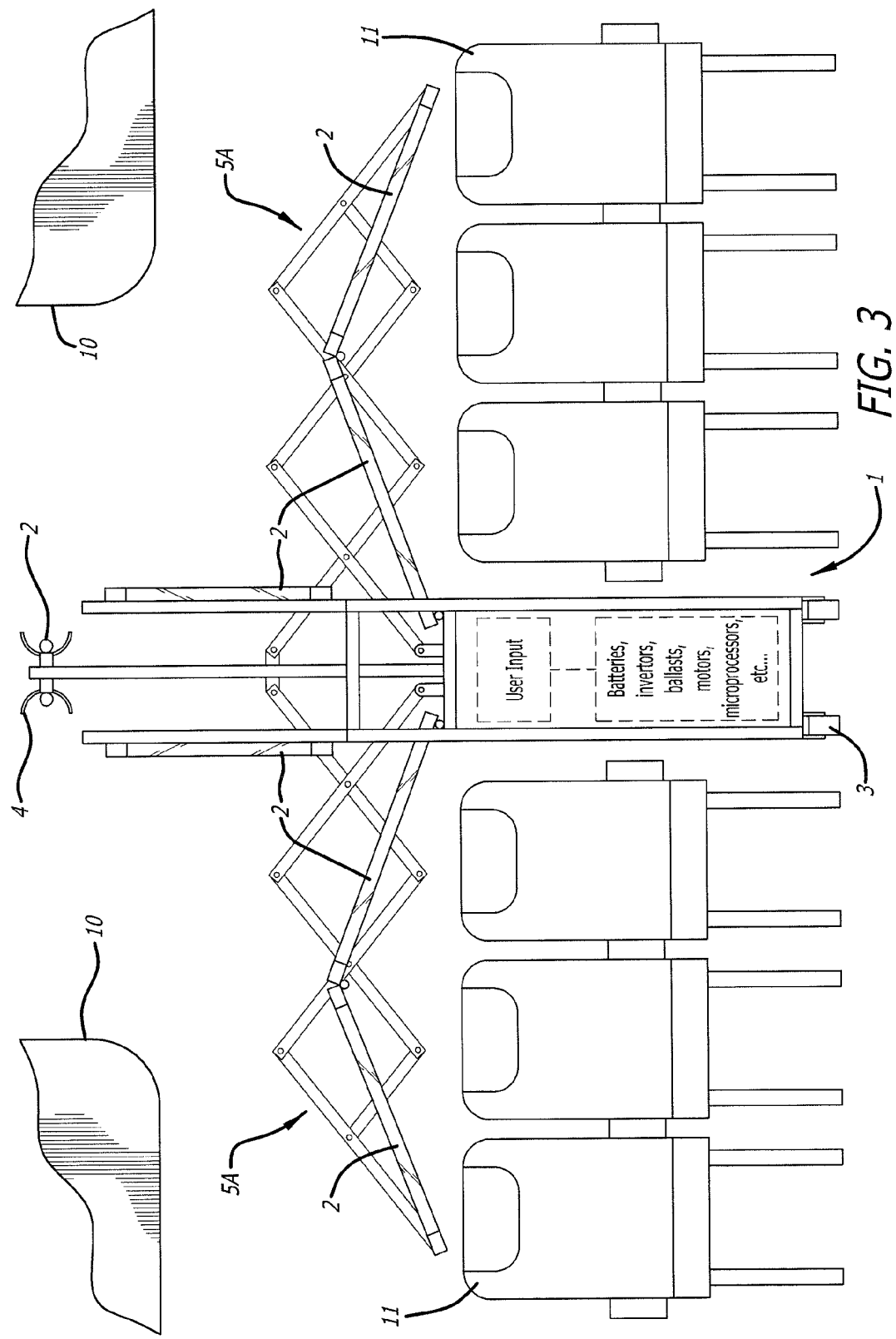
FIG. 3: Front View of Trolley with Arms Embodiment 1 in Fully Extended Positions.
Figure 4:
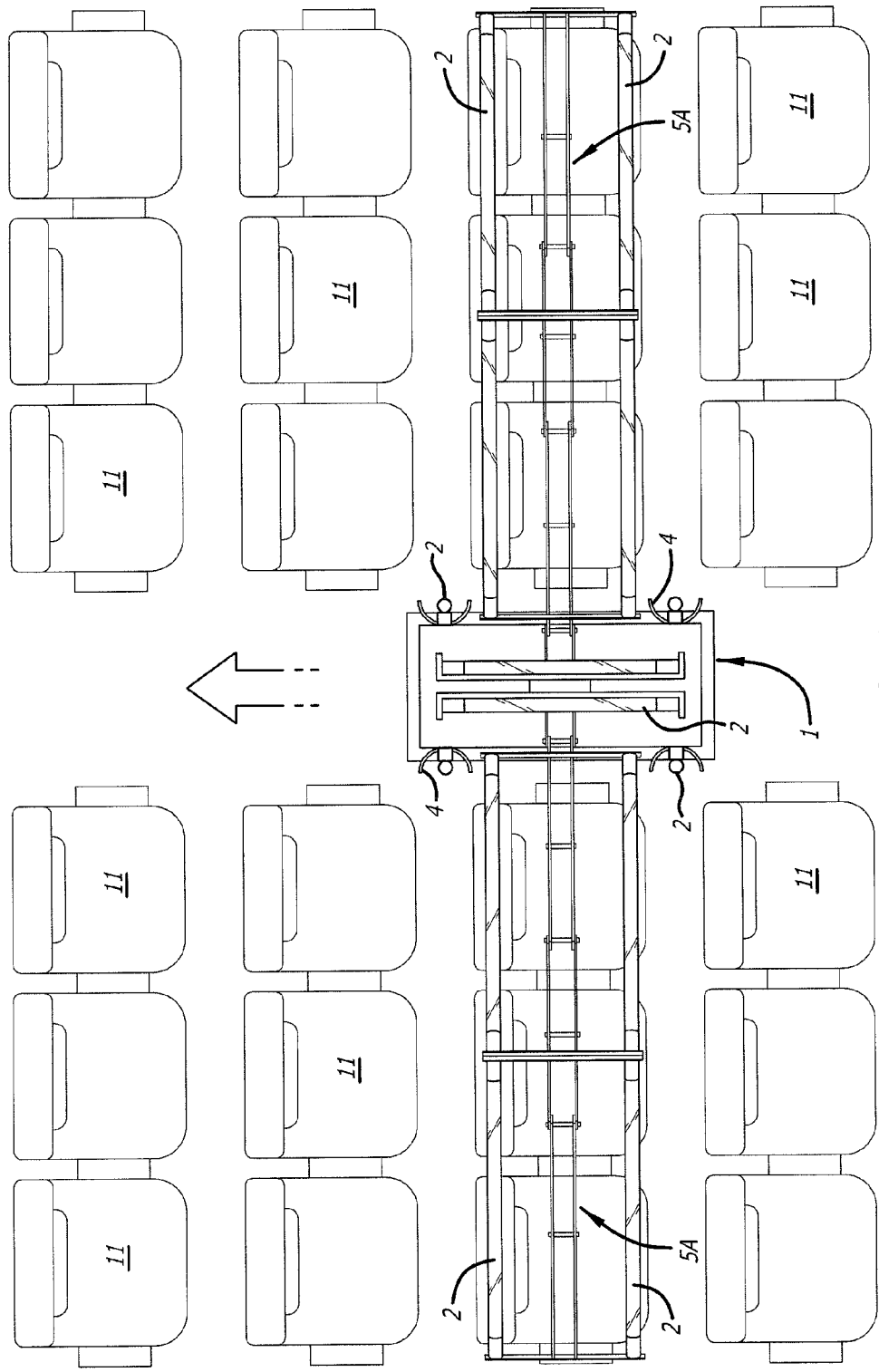
FIG. 4: Top View of Trolley with Arms Embodiment 1 in Fully Extended Positions.
Figure 5:
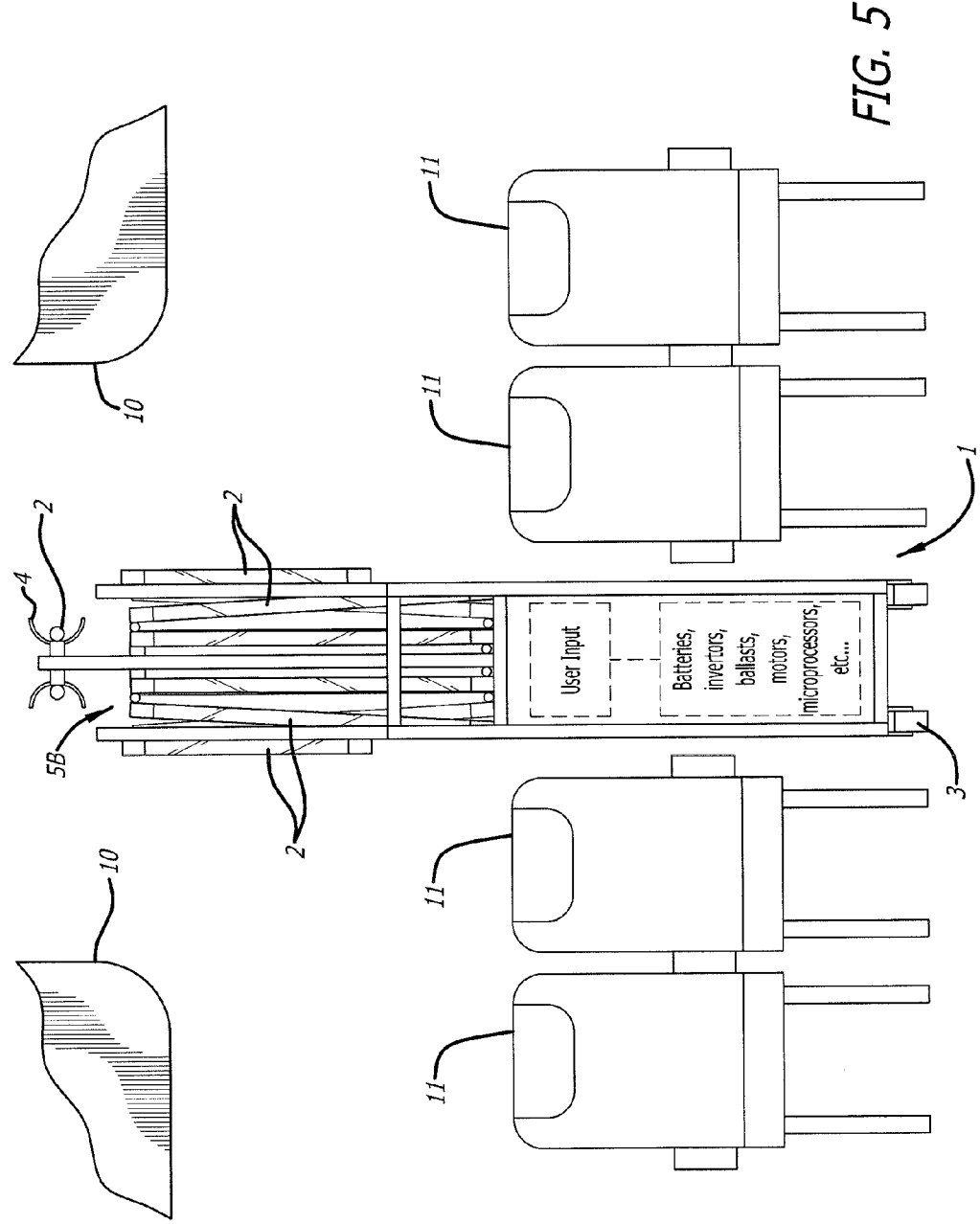
FIG. 5: Front View of Trolley with Arms Embodiment 2 in Stowed/Retracted Positions.
Figure 6:
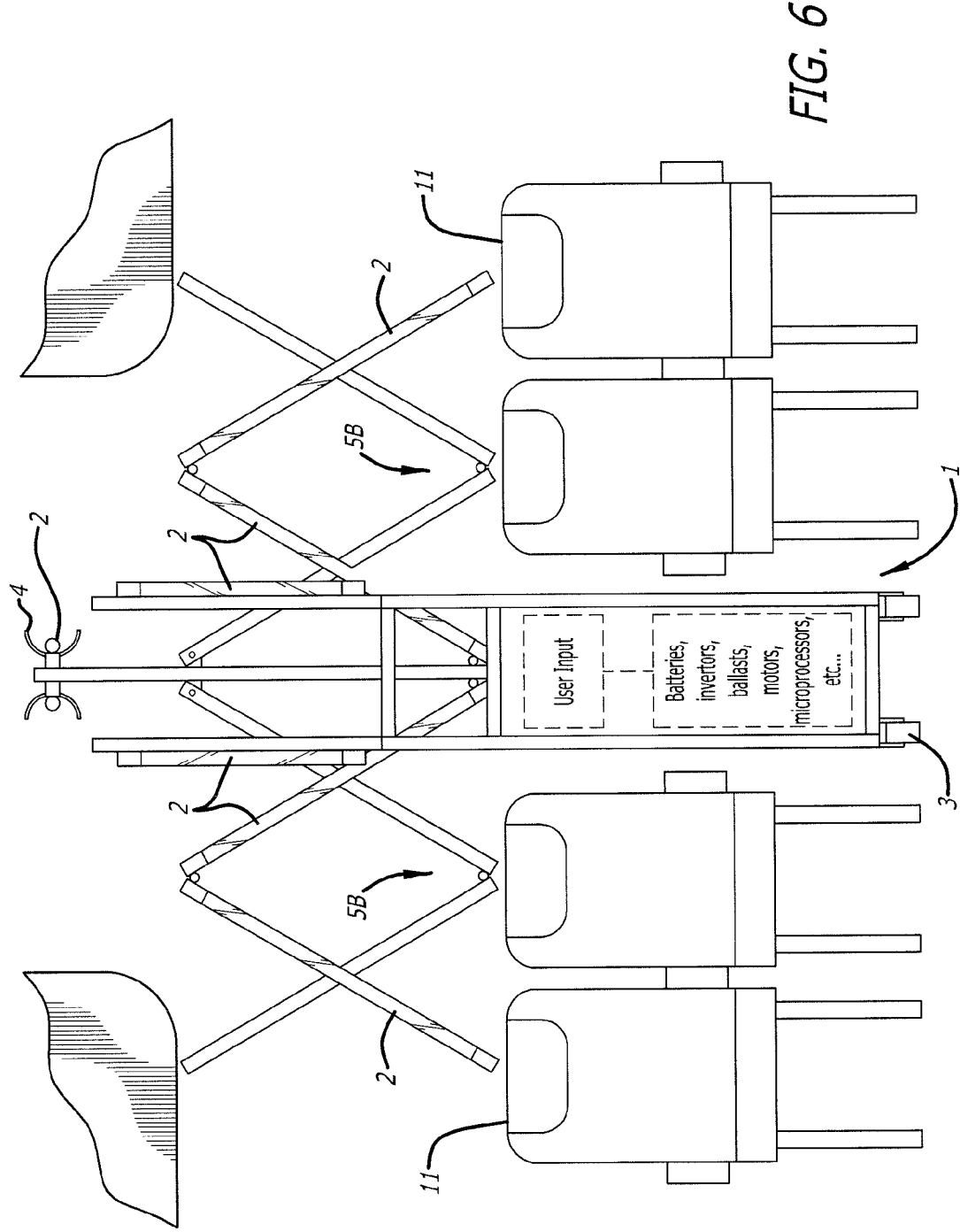
FIG. 6: Front View of Trolley with Arms Embodiment 2 in Partially Extended Positions.
Figure 7:
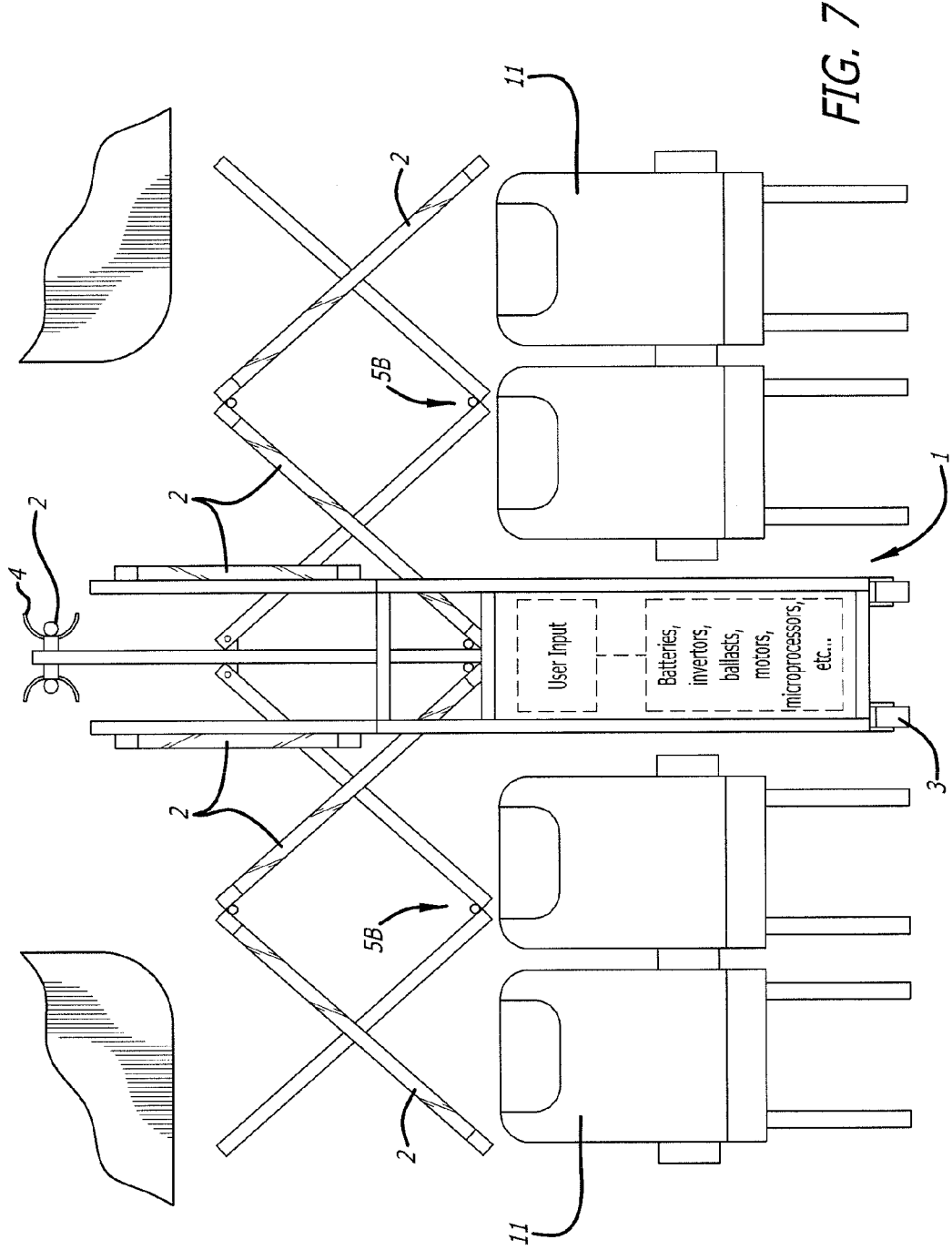
FIG. 7: Front view of Trolley with Arms Embodiment 2 in Greater Partially Extended Positions.
Figure 8:
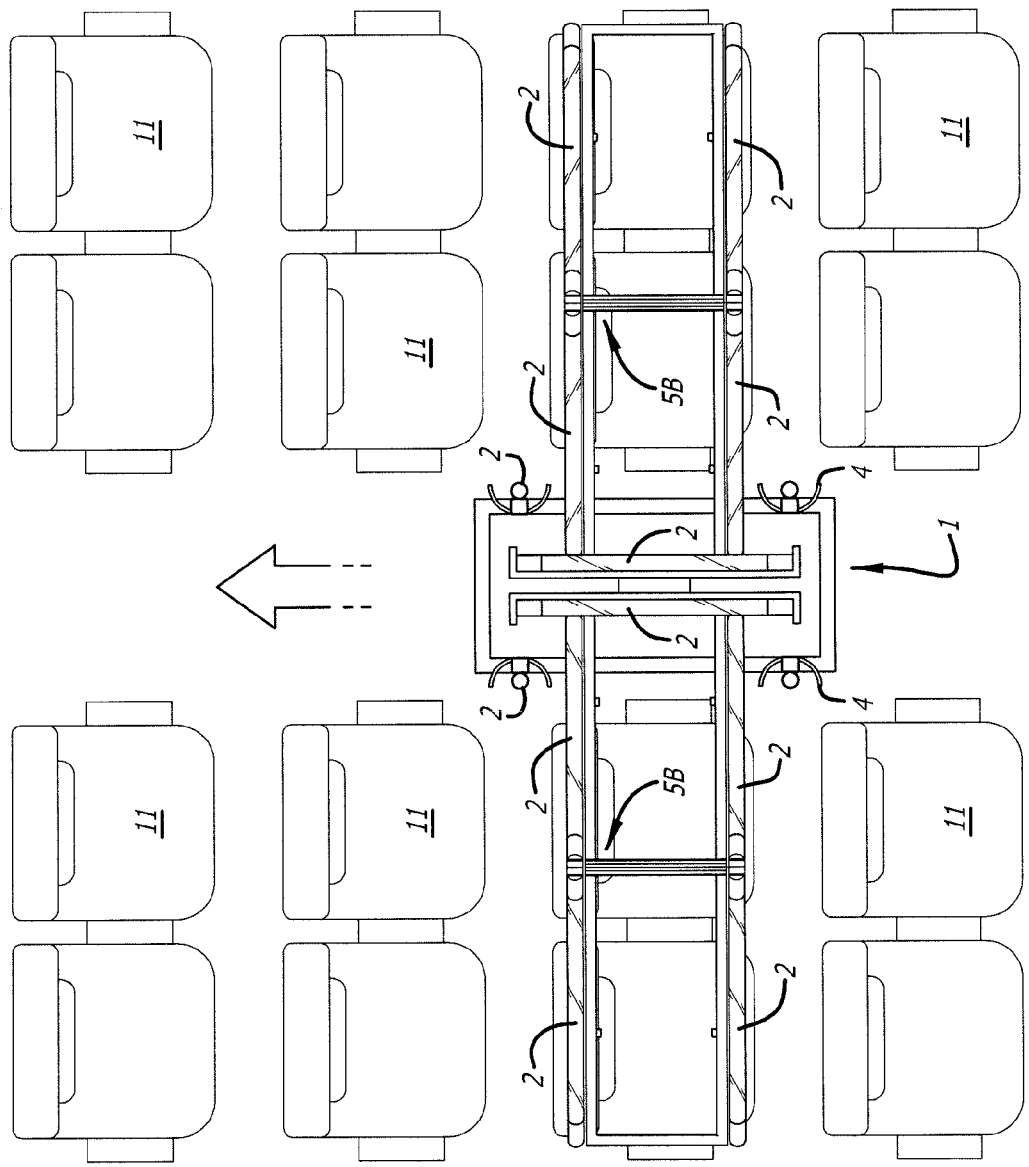
FIG. 8: Top View of Trolley with Arms Embodiment 2 in Fully Extended Positions.

The present disclosure generally relates to a sanitization device that utilizes a source of UV radiation to provide a means for sanitizing a surface. As will be discussed below in greater detail, embodiments of the sanitization device include a source of UV radiation in combination with a mobile body, or a housing for handheld operation. Additional embodiments of the present disclosure relate to methods of sanitizing surfaces using the sanitization devices of the present disclosure.

In accordance with another embodiment of the disclosure, the sanitization device includes a mobile body, a surface cleaning component, and a source of UV radiation. The surface cleaning component and the source of UV radiation are mounted to the mobile body, which is configured to travel over a surface. The surface cleaning component is configured to engage the surface and the source of UV radiation is configured to direct UV radiation to the surface.

In accordance with yet another embodiment of the disclosure, the sanitization device includes a housing, a source of UV radiation, and a sensor. The source of UV radiation is contained in the housing and positioned to transmit UV radiation through an opening in the housing. The sensor is configured to detect when the source is within a predetermined distance from a surface to be sanitized.

Additional embodiments of the present disclosure are directed to methods of using the above-identified sanitization devices to sanitize a surface.

A sanitization device for sanitizing a surface inside an aircraft cabin comprises a mobile body configured to travel over a surface. There is a source of UV radiation mounted to the mobile body and configured to direct UV radiation to the surface at a predetermined dosage. There are at least two articulated arms mounted to the mobile body, and UV lamps are mounted respectively on the arms. The mobile body is a trolley or cart for negotiating an aircraft aisle.

In another form there is a sanitization device for sanitizing a surface inside an aircraft cabin. There is a mobile body configured to travel over a surface; and a source of UV radiation mounted to the mobile body and configured to direct UV radiation to the surface at a predetermined dosage. At least one arm is mounted to the mobile body, and a UV lamp is mounted on the arm. The mobile body is a trolley or cart for negotiating an aircraft aisle.

The arm is movable from a position of storage with the mobile body to a position to extend from the mobile body wherein in the extended position the arm is operational to effect sanitization.

In one form each arm being for independent operation.

There are means for controlling motion of the arms over and about the aircraft surfaces, such surfaces including seats of the aircraft.

The arms are mounted with the mobile body and extendable from the mobile body at a position above the back rest of seats. The arms are movable over the seats and the UV lamps are directed to the seat surface as well as above the seats, and toward the interior sides of the fuselage.

The arm or arms are mounted with the mobile body and extendable from the mobile body at a position essentially solely above seats of an aircraft.

A surface cleaning component can be mounted to the mobile body and configured to engage the surface on which the mobile body travels.

The device includes a self-contained powering unit for powering the UV source.

The device can include a sensor for measuring the distance and or power the UV lamps relative to the surface and controlling the amount of and distance of the lamps from the surface and/or UV energy transmitted to the surface.

There is a method of sanitizing the seat surface in an aircraft cabin comprising the following steps. A sanitization device is provided to include a mobile body configured to travel along an aisle of an aircraft, and there is step of sanitizing with a device extending from the mobile device extendible across the seat surface.

There can be a surface cleaning component mounted to the mobile body and configured to engage the surface, A source of UV radiation mounted to the mobile body is moved so that the sanitization device is directed across the seat surface. The seat surface is exposed to UV radiation produced by the source, and the mobile body is moved along an aisle while the device travels over multiple seat surfaces.

A source of UV radiation mounted to the mobile body is directed to the seat surfaces at a predetermined dosage; extending at least one arm mounted to the mobile body with UV lamps mounted on the arm over the seats as the mobile body travels along an aircraft aisle. The mobile body is powered by a power source on board the mobile device.

The arm or arms are mounted on the mobile body and extend from the mobile body at least at a height above the seat level of the seat, and preferably between the seat level and the top of the backrest seat. The arms are preferably between the top of the backrest and the overhead bins.

A method of sanitizing includes a process wherein as the trolley moves on wheels along an aisle of an aircraft cabin, the arm is extended for movement in a space between the top of the cabin and above the top of backrest of the seats.

A method of sanitizing includes a process wherein as the trolley moves on wheels progressively along an aisle of an aircraft cabin, the arm is extended for movement in a space between the top of the cabin and progressively above the top of backrest of the seats and the seat portions of the seats.

Some different components of the system are set out:
1) Trolley
2) UVC source (lamp)
3) Trolley wheels
4) reflector
5) arm
6) arm extension retraction mechanism
7) rollers
8) hinges
9) guy wire
10) overhead bins
11) aircraft seats The trolley (1) has a "footprint" similar to that of a standard food/beverage trolley used on aircraft, but is of substantially greater height. The trolley has wheels (3), at least one of which is connected to a motor and at least one of which has a steering mechanism. The motor and steering mechanism are connected to an on-board microprocessor controller. There are proximity sensors, not illustrated, along the sides, fore and aft surfaces also connected to the controller.

Ultraviolet "C" (UVC) sources (2) are incorporated into all exterior fore, aft and side, and bottom surfaces of the trolley and located in a manner to maximize exposure of the aircraft interior surfaces. Reflectors (4) are utilized to maximize effective UVC output.

UVC laden "arms" (5) are connected to the trolley in such a manner to be variably laterally extensible above the aircraft seats (11) and below the overhead storage bins (10). These arms (5) may be retracted and stowed within the footprint of the trolley (1) for storage and when maneuvering the trolley (1) into position and on/off the aircraft. UVC source lamps (2) are also located in a sufficiently elevated position to expose the overhead storage bins (10).

Figure 9:
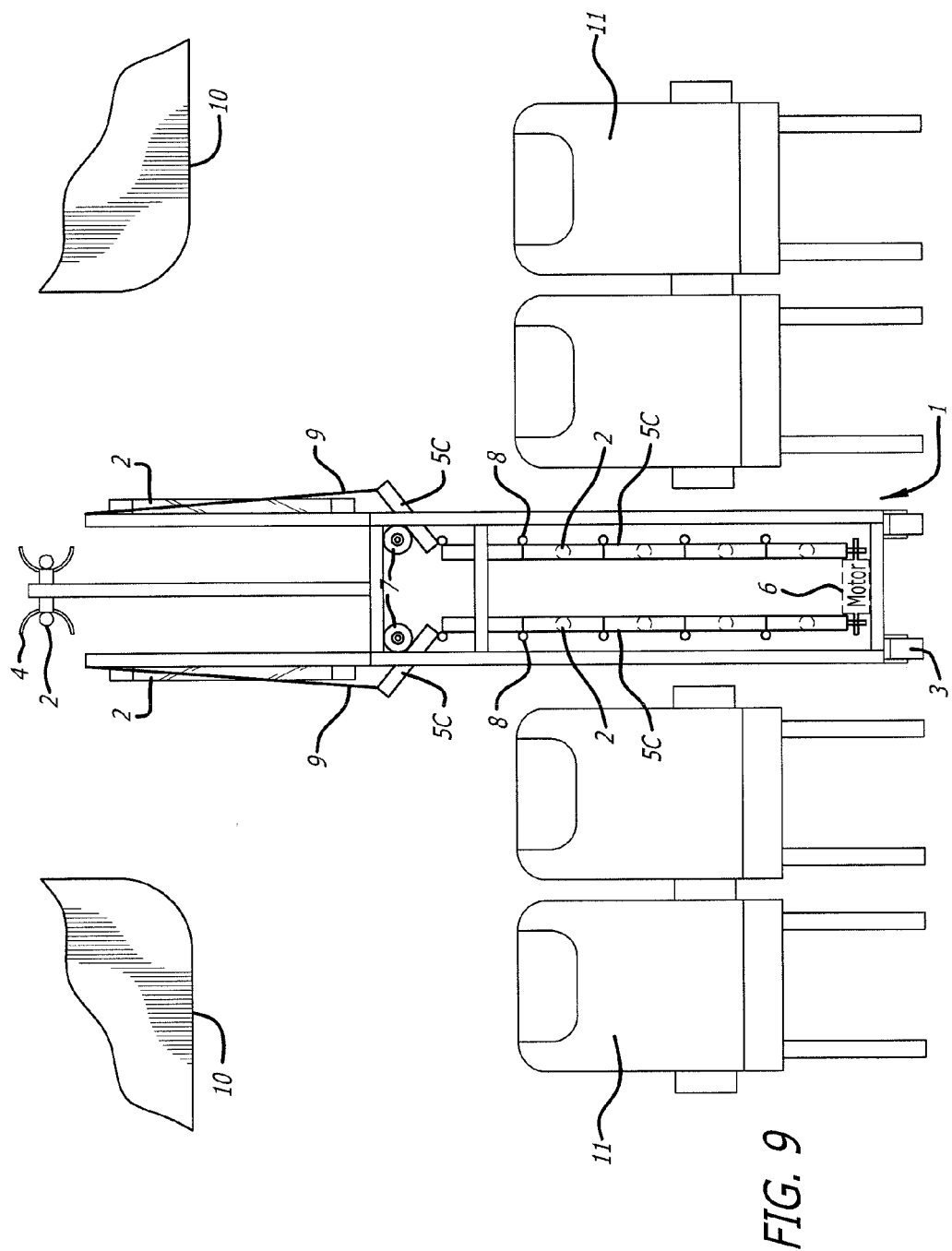
FIG. 9: Front View of Trolley with Arms Embodiment 3 in Stowed/Retracted Positions.
Figure 10:
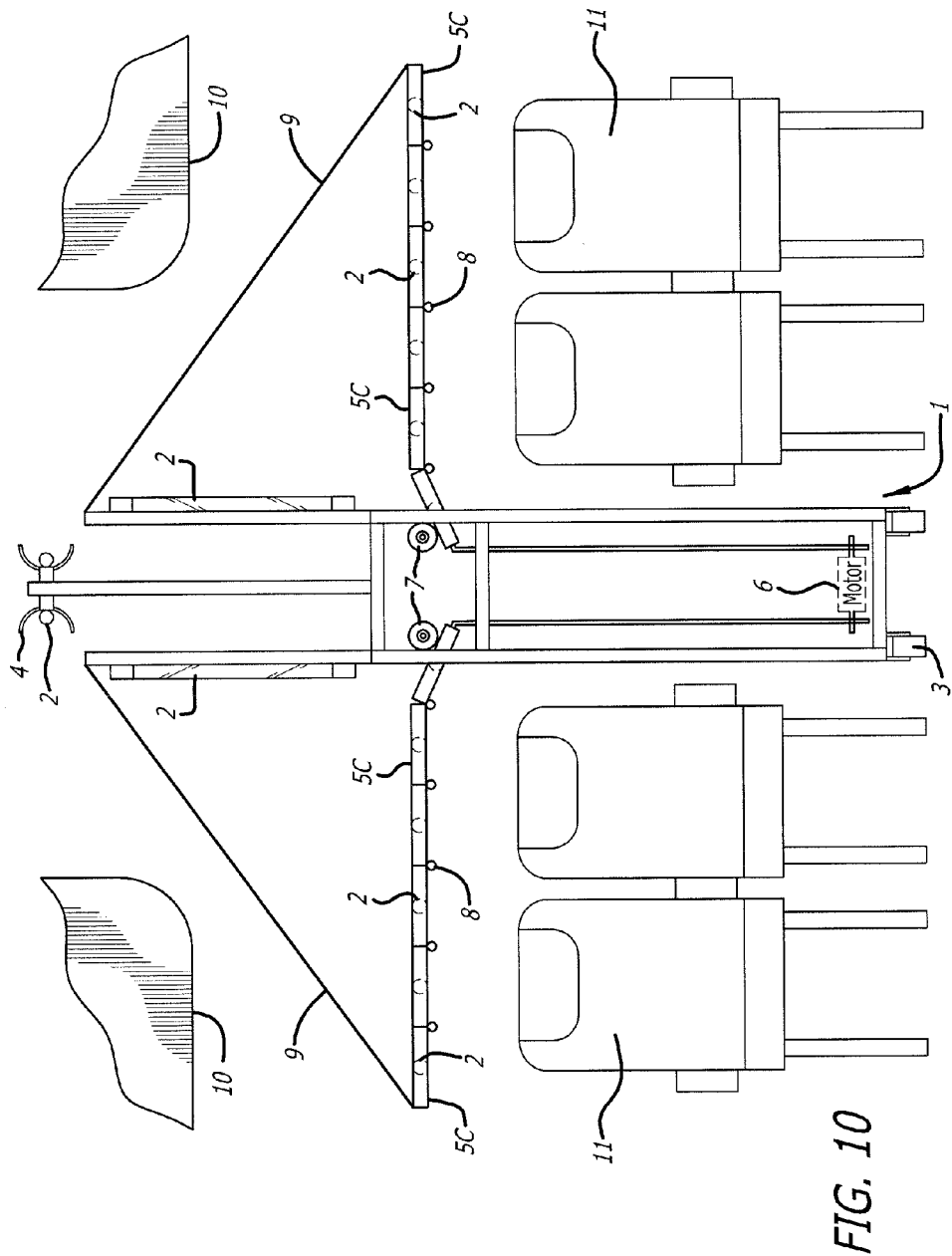
FIG. 10: Front View of Trolley with Arms Embodiment 3 in Fully Extended Positions.
Figure 11:
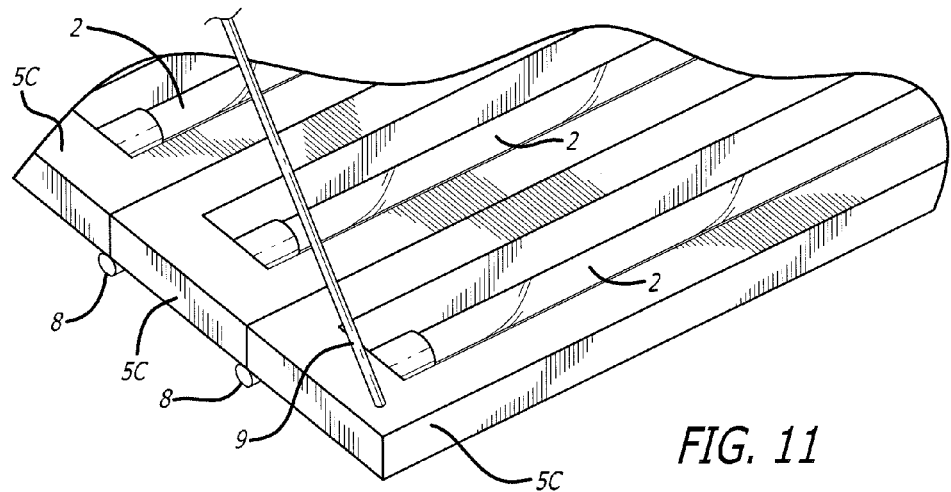
FIG. 11: Detail of Arm Embodiment 3 showing Lamps within Arm.
Figure 12:
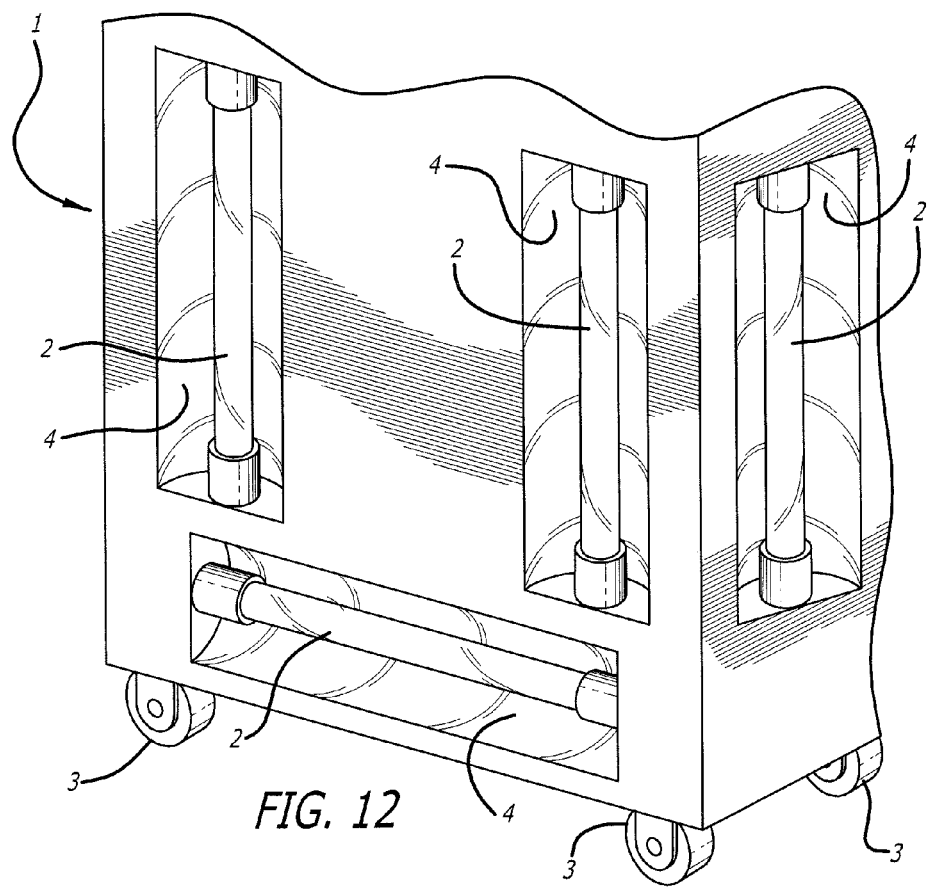
FIG. 12: Trolley Body with Recessed Lamps and Reflectors.

Arms (5) may be configured in a variety of embodiments. FIGS. 1-4 show arms (5) essentially a folding frame containing UVC Sources (2) attached to a scissors like extension/retraction mechanism (6). The extension/retraction mechanism (6) may be attached to a linear actuator, not illustrated, and motor controlled by the microprocessor. FIGS. 5-8 show an alternative arm embodiment wherein the UVC Sources (2) are directly embedded within the extension/retraction mechanism (6). FIGS. 9-11 show a "roll-up" type arm embodiment with UVC sources (2) embedded into the extension/retraction mechanism (6). For clarity of illustration, these arms (5) contain a limited number of UVC sources (2). Many more UVC sources (2) may be desirable depending upon the desired dose of UVC exposure and other constraints.

These multiple embodiments are not intended to be all inclusive, but rather demonstrative of the myriad ways that this disclosure can be constructed.

Vertical extensions with laterally directed UVC sources (2) also expose the overhead bins. The height of these sources may vary, depending upon aircraft configuration.

Fans, not illustrated for clarity, are also attached to the trolley (1) in such a manner to direct air flow into the path of UVC sources to sterilize the air. For example, fans directed laterally toward the floor can circulate air that might otherwise remain relatively stagnant. UVC light also generates ozone from ambient oxygen which helps deodorize the cabin as an additional benefit Rechargeable batteries are located within the trolley to power the motor, controller, steering mechanism, fans, arm extension mechanism and UVC sources. Some UVC lamps may also require ballast. These heavier components are preferentially located at the lower portion of the trolley to maximize lateral anti-tip-over stability. A power cord port, not illustrated, allows plug in charging when the trolley is not in use.

Operation:

The trolley (1) is stowed off the aircraft, with arms (5) retracted, and plugged into an external power source to charge the on-board batteries. When ready for use, the apparatus of this disclosure is unplugged and wheeled onto the aircraft in a manner similar to known food/beverage trolleys. The trolley is positioned in the aisle between the first row (or last row) of seats. The arms (5) are extended utilizing the extension/retraction (6) mechanism. The UVC sources (2) are powered on with a delay mechanism sufficient to allow personnel to leave the aircraft, or remotely. The trolley (1) proceeds along the aisle, autonomously centered by the lateral proximity sensors and the wheel (3) steering mechanism. The apparatus of this disclosure proceeds autonomously to the last row (or first row) of seats, detected by the aft proximity sensors or pre-programmed by the number of rows. The trolley (1) stops, reverses direction and proceeds in the opposite direction in the aisle to the starting point.

The trolley (1) speed of travel may be programmed and is dependent upon the UVC source output, distance from UVC source to surface, and desired level of kill rate. Kill rates are dose dependent, measured in Wsec/m2 and specific microbial sensitivities are known. The total treatment duration should conform to other ground turn-around time constraints for the aircraft.

When treatment is completed, the arms (5) are retracted to the stowed position. The apparatus of this disclosure is then transported back to the storage facility and plugged back into the external power source.

Some Alternative Embodiments

The foregoing describes the minimum configuration of the current disclosure. A multitude of additions and variations are anticipated beyond this basic description. The following are representative examples of alternative embodiments and additional features, but are not intended to be all inclusive.

UVC sources may be fluorescent lamps, Light Emitting Diodes (LED), pulsed Xenon and other technologies known to produce ultraviolet light in the germicidal range.

The trolley has an estimated weight of approximately 75 pounds. A motor assist for pushing the trolley may be incorporated to ease in its mobility on and off the aircraft.

The UVC laden arms are foldable to substantially within the "footprint" of the trolley during transportation on and off the aircraft and for stowage. The arms extend laterally and perpendicular to the aisle at variable distance from the trolley. The two arms extend laterally independently to accommodate asymmetric seating configurations. There are a multitude of known mechanisms that allow this feature and some are illustrated within this application. More elaborate telescoping/folding/rolling or otherwise extensible mechanisms can be incorporated into the design and the disclosure includes such variations. The arms function independently of each other to optimally treat aircraft that may have different numbers of seats on each side of the aisle.

Because UVC light is potentially damaging to human skin and eyes, an onboard detection, warning and abort system is preferred. Sensors that monitor motion and heat or visual pattern recognition can be incorporated to detect human presence within a potentially dangerous radius of the device. Audible and visible alarms alert the human to the potential danger. The device stops and the UVC sources are depowered to prevent possible injury. Similarly cameras can be included to remotely monitor the trolley's progress. UVC does not penetrate clothing, plastics or glass and very simple personal protective gear covering all skin and a simple visor would allow a worker to be safely adjacent to the trolley.

Programming may involve varying levels of automation. For example, one may program for the cabin of a 777 aircraft and the controller determines the direction, speed, number of rows, the desired extension of the arms and height of the UVC sources for the overhead bins. Less sophisticated programming may have variable row numbers, seats per row, speed of trolley travel, depending upon level of contamination etc.

A more sophisticated travel path may also be anticipated and programmed. For example, the arms may be programmed to follow the contours of the passenger seat, going up and down around the seat backs and even down to the floor to bring the UVC sources into closer proximity to contaminated sources.

In the method, the device and apparatus is positioned to expose the UV source in a positioned to expose the components of the aircraft desired to be sanitized. There can also be a cleaning component with the apparatus and a waste container or tank with the device. The exposure of the cleaning component and the interior of the waste container or tank, operates to control the proliferation of microorganisms and the generation of odor.

The extensible arms have the ability to disinfect surfaces that are not traveled over, but are remote from the traveled surface. Those surfaces, like seats, seat backs and tray tables cannot be traveled over and could not be sanitized are sanitized by the disclosed device which has those extensible arms.

An alternative embodiment could have the arms going up and down between seatbacks as the device travels in the aisle to get the arms closer to the sitting surface.

Surfaces like seats, seat backs and tray tables cannot be traveled over. Such surfaces could not be sanitized by a device that directs UV radiation to the surface on which it travels. The disclosed device, with extensible arms, allows such surfaces to be sanitized.

An alternative embodiment could have the arms going up and down between seatbacks as the device travels in the aisle to get the arms closer to the seat surfaces.

An alternative embodiment is a permanent installation onboard an aircraft with a storage compartment. There can be a configuration of the disclosure where the device would be stowed in a closed compartment and rather than wheels, for example a ceiling mounted rail system allows the device to travel fore and aft in the passenger compartment. An advantage to this system is that the aircraft can be sanitized regardless of whether the airport has functioning devices. A further advantage is apparent in case of an on-board inflight release of a pathogen, whether accidental/unintentional or bioterrorism. By activating an onboard device, with passengers shielded, an aircraft can be "sanitized" inflight prior to landing. This would avoid release of potential pathogens at the destination and neutralize the threat prior to human inoculation.

Many different formats are possible for the disclosure. It is therefore to be understood that within the scope of the appended claims the disclosure may be practiced otherwise than as specifically described.

What is claimed is:

1. A sanitization device for sanitizing a surface inside an aircraft cabin comprising: a mobile body configured to travel over a surface; and a source of UV radiation mounted to the mobile body and configured to direct UV radiation to the surface at a predetermined dosage; at least two articulated arms mounted to the mobile body, UV lamps mounted respectively on the arms, the mobile body being a trolley or cart for negotiating an aircraft aisle, and a power source for activating the UV radiation as the trolley or cart moves along the aircraft aisle, and wherein the two articulated arms are mounted with the mobile body and extendable from the mobile body at a position movable over the seats and the UV lamps are directed to the seat surface, are when extended from the mobile body and back into mobile body are above seat level, wherein the multiple UV lamps are set up in end to end relationship, and wherein the arms for the lamps are foldable inwardly relative to each other and towards the trolley and outwardly from each other and from the trolley to extend over the seats, the folding being through a hinge located with each of the arms.

2. A sanitization device for sanitizing a surface inside an aircraft cabin comprising: a mobile body configured to travel over a surface; and a source of UV radiation mounted to the mobile body and configured to direct UV radiation to the surface at a predetermined dosage; at least one arm mounted to the mobile body, a UV lamp mounted on the arm, and the mobile body being a trolley or cart for negotiating an aircraft aisle, wherein the arm is movable from a position of storage with the mobile body to a position to extended from the mobile body wherein in the extended position the arm is operational to effect sanitization, a power source for activating the UV radiation as the trolley or cart moves along the aircraft aisle, and the arm being mounted on the side of the trolley or cart, and the arm includes multiple UV lamps mounted on the arm in spaced relationship with each other thereby in the extended position to cover an increased area to effect sanitation, and wherein the arm is mounted with the mobile body and extendable from the mobile body at a position movable over the seats and the UV lamps are directed to the seat surface, and when extended from the mobile body and back into mobile body are above the seat level, wherein the multiple UV lamps are set up in end to end relationship, and wherein the arm for the lamps is foldable inwardly and towards the trolley and outwardly from the trolley to extend over the seats, the folding being through a hinge located with the arm.

3. The device of claim 1 wherein each arm being for independent operation.

4. The device of claim 1 including means for controlling motion of the arms over and about the aircraft surfaces, such surfaces including seats of the aircraft.

5. The device as claimed in claim 1 wherein the arms are mounted with the mobile body and extendable from the mobile body at a position above the back rest of seats, and is movable over the seats and the UV lamps are directed to the seat surface.

6. The device as claimed in claim 2 wherein the arm is mounted with the mobile body and extendable from the mobile body at a position above the back rest of seats, and is movable over the seats and the UV lamps are directed to the seat surface.

7. The device as claimed in claim 1 wherein the arms are mounted with the mobile body and extendable from the mobile body at a position essentially solely above seats of an aircraft, and is movable over the seats and the UV lamps are directed to the seat surface.

8. The device as claimed in claim 2 wherein the arm is mounted with the mobile body and extendable from the mobile body at a position essentially solely above seats of the aircraft, and is movable over the seats and the UV lamps are directed to the seat surface.

9. The device of claim 1 including a surface cleaning component mounted to the mobile body and configured to engage the surface on which the mobile body travels.

10. The device of claim 1, including a self-contained powering unit for powering the UV source.

11. The device of claim 1, wherein each arm is independently extendible and operational over and around the seat surfaces.

12. The device of claim 1, including a sensor for measuring the distance and or power the UV lamps relative to the surface and controlling the amount of and distance of the lamps from the surface and/or UV energy transmitted to the surface.

13. The device of claim 1, wherein the arms are mounted on the mobile body and extend from the mobile body at least at a height above the seat level of the seat, and preferably between the seat level and the top of the backrest of the seat, or preferably above the top of the back rest of the seat and below overhead bins of the aircraft, and including hinges between the trolley and arms whereby during storage the arms are folded into the trolley such that the arms are entirely at a position above the seat level.

14. The device as claimed in claim 2 wherein the arm is mounted with the mobile body and extendable from the mobile body at a position essentially solely above seats of an aircraft, and is movable over the seats and the UV lamps are directed to the seat surface, and when extended from the mobile body and back into mobile body are maintained solely above the seat level, such that the UV lamps are located entirely in an upper portion of the mobile body, and removed from a lower portion of the mobile body.

15. The device as claimed in claim 2 wherein the arm is mounted with the mobile body and extendable from the mobile body at a position above seats of an aircraft, and is movable over the seats and the UV lamps are directed to the seat surface, and when extended from the mobile body and back into mobile body are maintained above the seat level, such that the UV lamps are located in a relatively upper portion of the mobile body; and including a hinge between the arm and the mobile body, the hinge permitting the upward movement of the arm between an extended position, selectively horizontal position, and an upward position essentially over a body of the mobile body.

16. The device as claimed in claim 2 wherein the arm is mounted with the mobile body and extendable from the mobile body at a position movable over the seats and the UV lamps are directed to the seat surface, and when extended from the mobile body and back into mobile body are above the seat level, such that the UV lamps are located in an upper portion of the mobile body, and wherein the multiple UV lamps are set up in end to end or array relationship.

17. The device as claimed in claim 14 wherein the arm is mounted with the mobile body and extendable from the mobile body at a position movable over the seats and the UV lamps are directed to the seat surface, and when extended from the mobile body and back into mobile body are above the seat level, such that the UV lamps are located in an upper portion of the mobile body, and wherein the multiple UV lamps are set up in an end to end or array relationship.

18. The device as claimed in claim 1 including a motor for the mobile body and wherein the mobile body is steerable for negotiating an aircraft aisle.

19. The device as claimed in claim 2 including a motor for the mobile body and wherein the mobile body is steerable for negotiating an aircraft aisle.

20. A sanitization device for sanitizing a surface inside an aircraft cabin comprising: a mobile body configured to travel over a surface; and a source of UV radiation and configured to direct UV radiation to the surface at a predetermined dosage; at least two articulated arms mounted to the mobile body, UV lamps mounted respectively on the arms, the mobile body being a trolley or cart for negotiating an aircraft aisle, and a power source for activating the UV radiation as the trolley or cart moves along the aircraft aisle wherein the arms are mounted on the mobile body and extend from the mobile body at least at a height above the seat level of the seat, and hinges located in a position with the trolley and with the arms for the UV radiation sources such that the arms are foldable towards the trolley during storage action, and when the arms are folded into the trolley, the arms are entirely at a position above the seat level, and the trolley further including multiple spaced UV radiation lamps located in relatively spaced fixed positions in and around the trolley body for projecting UV radiation from the trolley body, and wherein the two arms are mounted with the mobile body and extendable from the mobile body at a position movable over the seats and the UV lamps are directed to the seat surface, and when extended from the mobile body and back into mobile body are above the seat level, wherein the multiple UV lamps are set up in end to end relationship, and wherein the arms for the lamps are foldable inwardly relative to each other and towards the trolley and outwardly from each other and from the trolley to extend over the seats, the folding being through hinge located with each arm.

* * * * *